United States Patent [19]
Miraki

[11] Patent Number: 5,389,087
[45] Date of Patent: * Feb. 14, 1995

[54] FULLY EXCHANGEABLE OVER-THE-WIRE CATHETER WITH RIP SEAM AND GATED SIDE PORT

[75] Inventor: Manouchehr Miraki, Aliso Viejo, Calif.

[73] Assignee: Baxter International Inc., Deerfield, Ill.

[*] Notice: The portion of the term of this patent subsequent to Jun. 28, 2011 has been disclaimed.

[21] Appl. No.: 907,132

[22] Filed: Jun. 29, 1992

Related U.S. Application Data

[63] Continuation-in-part of Ser. No. 893,588, Jun. 2, 1992, Pat. No. 5,324,269, which is a continuation of Ser. No. 762,827, Sep. 19, 1991, abandoned.

[51] Int. Cl.$^6$ ............................................. A61M 5/00
[52] U.S. Cl. ...................................... 604/247; 604/96; 604/160
[58] Field of Search .................. 604/43, 96, 247, 280, 604/286, 246, 236, 238, 237, 160

[56] References Cited

U.S. PATENT DOCUMENTS

| | | |
|---|---|---|
| 705,346 | 7/1902 | Hamilton . |
| 1,690,995 | 11/1928 | Pratt . |
| 3,726,283 | 4/1973 | Dye et al. ............... 604/247 |
| 3,742,960 | 7/1973 | Dye et al. ............... 604/247 |
| 3,853,130 | 12/1974 | Sheridan . |
| 4,175,564 | 11/1979 | Kwak . |
| 4,552,554 | 11/1985 | Gould et al. . |
| 4,569,347 | 2/1986 | Frisbie . |
| 4,589,869 | 5/1986 | Wernborg ............... 604/247 |
| 4,652,258 | 3/1987 | Drach . |
| 4,748,982 | 6/1988 | Horzewski et al. . |
| 4,762,129 | 8/1988 | Bonzel . |
| 4,881,547 | 11/1989 | Danforth . |
| 4,943,278 | 7/1990 | Euteneuer et al. . |
| 4,944,745 | 7/1990 | Sogard et al. . |
| 4,976,690 | 12/1990 | Solar et al. . |
| 4,988,356 | 1/1991 | Crittenden et al. . |
| 4,995,863 | 2/1991 | Nichols et al. ............ 604/247 |
| 5,030,210 | 7/1991 | Alchas ............... 604/247 |
| 5,135,535 | 8/1992 | Kramer . |
| 5,156,600 | 10/1992 | Young ............... 604/247 |

FOREIGN PATENT DOCUMENTS

| | | |
|---|---|---|
| 93887A | 11/1983 | European Pat. Off. . |
| 121533A | 10/1984 | European Pat. Off. . |
| 0166212 | 1/1986 | European Pat. Off. . |
| 249456A | 12/1987 | European Pat. Off. . |
| 299158A | 1/1989 | European Pat. Off. . |
| 309754A | 4/1989 | European Pat. Off. . |
| 321648A | 6/1989 | European Pat. Off. . |
| 0380873 | 8/1990 | European Pat. Off. . |
| 386408A | 9/1990 | European Pat. Off. . |
| 0388112 | 9/1990 | European Pat. Off. . |
| 399712A | 11/1990 | European Pat. Off. . |
| 420486A | 4/1991 | European Pat. Off. . |
| 0434324 | 6/1991 | European Pat. Off. . |
| 0435157 | 7/1991 | European Pat. Off. . |
| 2597350 | 4/1987 | France . |
| 3320710A | 12/1983 | Germany . |
| 395579A | 5/1991 | Germany . |
| 2033236 | 5/1980 | United Kingdom . |
| WO86/01414 | 3/1986 | WIPO . |
| WO86/07267 | 12/1986 | WIPO . |
| WO88/00071 | 1/1988 | WIPO . |

*Primary Examiner*—Paul J. Hirsch
*Attorney, Agent, or Firm*—Poms Smith Lande & Rose

[57] ABSTRACT

A fully exchangeable over-the-wire catheter is disclosed having a lumen adapted to slidingly receive a guidewire throughout the longitudinal extent of the tubular shaft. The tubular shaft may also be provided with a longitudinal rip seam extending into the lumen from the proximal portion of the tubular shaft to a point adjacent the distal end of the tubular shaft which enables the catheter to be peeled from the guidewire during removal and exchange procedures without the need for docking a guidewire extension. The catheter may be provided with one or more side access ports into the guidewire lumen which may include angled partitions to control guidewire routing. The guidewire may be threaded through the side access ports in a variety of manners as desired.

23 Claims, 6 Drawing Sheets

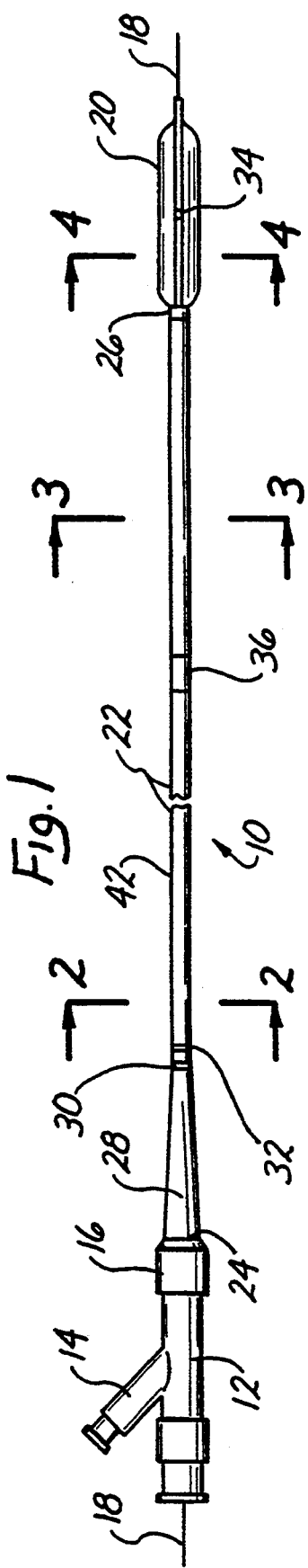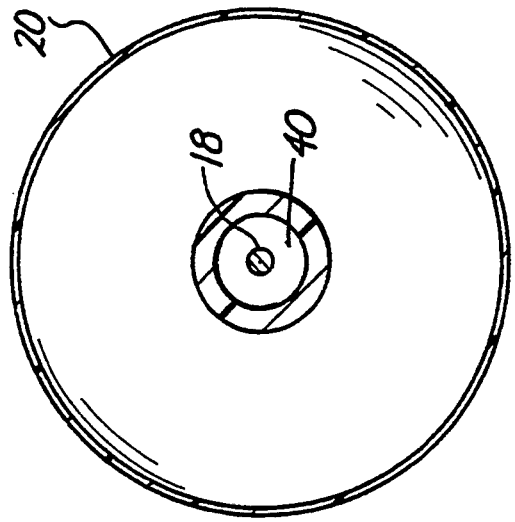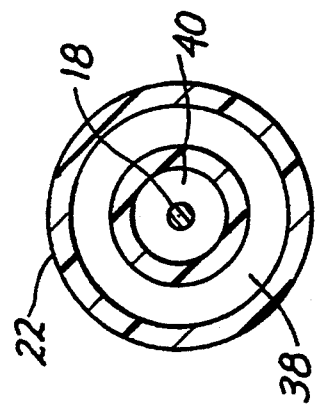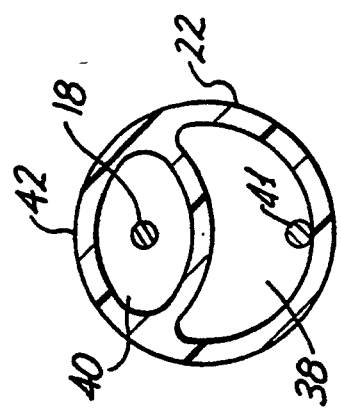

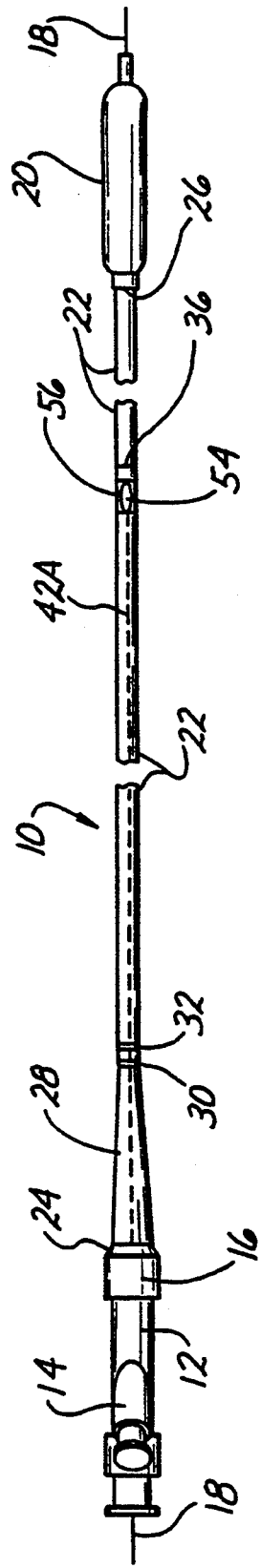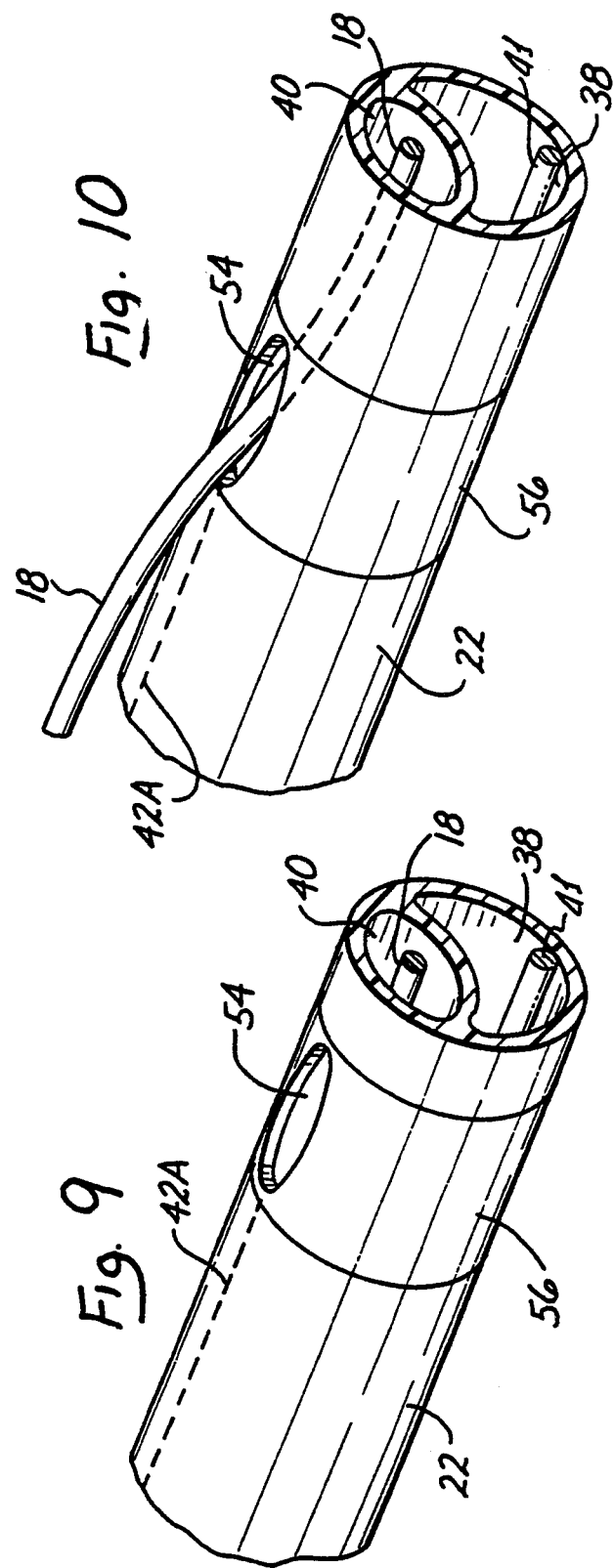

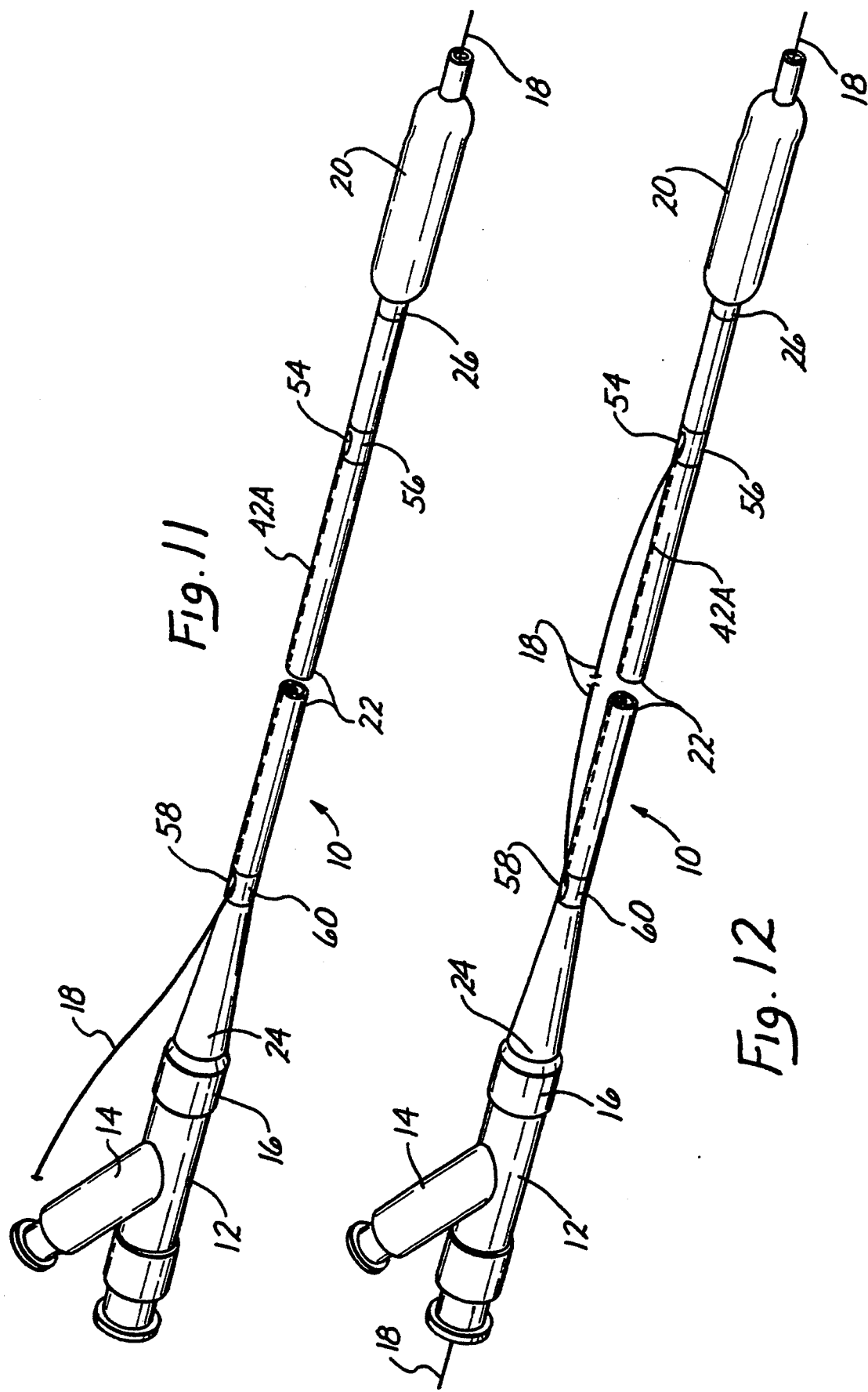

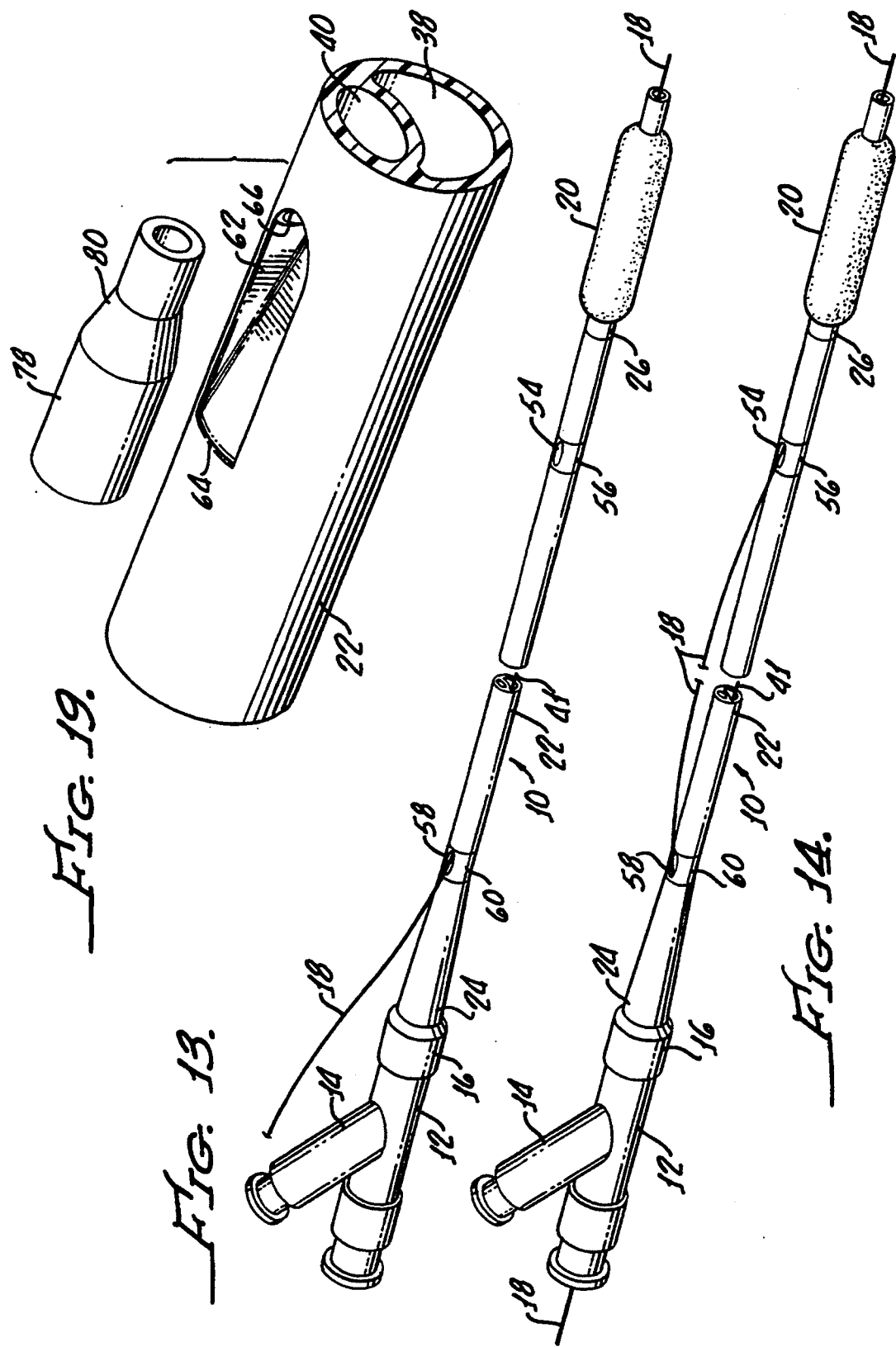

FULLY EXCHANGEABLE OVER-THE-WIRE CATHETER WITH RIP SEAM AND GATED SIDE PORT

Reference to Prior Application

This is a continuation-in-part of application Ser. No. 07/893,588, filed on Jun. 2, 1992, now U.S. Pat. No. 5,324,269, which is a continuation of application Ser. No. 07/762,827, filed on Sep. 19, 1991, now abandoned.

FIELD OF THE INVENTION

The present invention relates in general to the field of dilatation or balloon catheters employed in the treatment of vascular diseases. More particularly, the present invention relates to an over-the-wire balloon catheter that may be provided with a longitudinal rip seam extending along a majority of the length of its guidewire lumen from its proximal opening or adjacent thereto to a position adjacent its distal end or its dilatation balloon to facilitate the removal or exchange of the catheter assembly without docking a guidewire extension. Further, the guidewire lumen may include one or more gated or non-gated side ports to facilitate or control guidewire routing during placement or exchange of the catheter or its associated guidewire.

BACKGROUND OF THE INVENTION

A principal goal of modern medicine has been the reduction of trauma associated with various surgical procedures. When surgical invasiveness and trauma are reduced the associated surgical complications are correspondingly reduced. As a result, the less invasive the surgical procedure the greater the chances for a rapid, uncomplicated recovery. A recent successful development in the field of less invasive surgery is the medical procedure known as angioplasty. Angioplasty has become a widely accepted method for opening obstructions or stenoses throughout the vascular system, particularly in the coronary arteries.

The most common form of angioplasty practiced to date is known as percutaneous transluminal coronary angioplasty (PTCA). In virtually all forms of this procedure a dilatation catheter having an inflatable balloon at its distal end is guided through the patient's artery and the balloon is positioned across the stenosis. Once in place the balloon is inflated for a brief period of time in order to displace or deform the occluding lesion. After the stenosis has been opened and adequate blood flow has been reestablished the catheter is withdrawn. In this manner, it is possible to open blocked coronary arteries through a small vascular incision without the serious risks and complications previously associated with open heart surgery.

In most forms of angioplasty the dilatation catheter is guided into position through the patient's arteries utilizing a very small diameter flexible guidewire. Typically, guidewires are formed of surgical grade stainless steel having a diameter on the order of 0.010 to 0.015 inches and an overall length of approximately 175 cm. The distal end of the guidewire is extremely flexible and may be formed as a coil of very small diameter wire to enable the cardiac physician to direct the guidewire along the branched and convoluted arterial pathway as the guidewire is advanced to the target site. Once the guidewire is positioned across the lesion an appropriately sized dilatation catheter is advanced "over-the-wire".

At this point in the procedure the dilatation balloon is in a deflated configuration having a minimal cross-sectional diameter which facilitates its positioning across the lesion prior to inflation. At various times throughout the procedure radiopaque dyes are injected into the artery to enable the cardiac physician to visualize the catheter and target vascular pathway on a fluoroscope.

An undesirable complication associated with the utilization of such "over-the-wire" dilatation catheters is the need to extend the guidewire outside of the patient's body a sufficient distance to enable the over-the-wire catheter to be threaded onto the guidewire without disturbing the positioning of the guidewire across the target lesion. Typically, a guidewire extension is "docked" or affixed to the proximal end of the guidewire in order to provide the additional length necessary to thread the guidewire into the catheter. As the typical dilatation catheter ranges in length from 120 cm to 160 cm the guidewire extension can be quite long and awkward to manipulate as it extends outside the patient's body. Alternatively, an exceptionally long guidewire on the order of 300 cm in length may be positioned initially and subsequently exchanged with a shorter, easier to handle guidewire after positioning of the catheter. In either case, an additional medical assistant may be necessary solely to monitor or manipulate the guidewire or its extension. Moreover, the junction between the docked guidewire end and the docked extension may interfere with the smooth advancement of the catheter along the guidewire decreasing the physician's control of the procedure.

A number of alternative dilatation catheter designs have been developed in an attempt to reduce or eliminate these problems. For example, "fixed-wire" dilatation catheters incorporating an internally fixed guidewire or stiffening element have been utilized with some degree of success. In addition to eliminating the need for guidewire extensions, these fixed-wire designs are smaller in diameter than their over-the-wire counterparts because the balloon inflation lumen is also utilized to contain the fixed guidewire. As a result, these designs are quite maneuverable and relatively easy to position. However, the most significant drawback associated with fixed-wire catheter designs is the inability to retain guidewire access to the target site while removing the catheter. Removal or replacement of a balloon catheter is not an uncommon occurrence during balloon angioplasty. Should it become necessary to perform such a removal or exchange procedure the fixed guidewire also must be removed simultaneously. This greatly complicates reaccessing the lesion with a subsequent device if desired.

Similarly, an additional drawback of fixed-wire catheter designs is the inability to exchange the guidewire. Though relatively rare, replacement of a guidewire is sometimes required when the original wire is broken or defective, or when the wire tip must be reshaped to perform the procedure. With these fixed wire unitary designs the entire assembly must be removed forcing the vascular physician to renegotiate the arterial pathway with a new catheter and guidewire combination.

An alternative catheter design is the "monorail" variant of the over-the-wire system such as that disclosed in U.S. Pat. No. 4,762,129 issued Aug. 9, 1988 to Bonzel. This catheter design utilizes a conventional inflation lumen plus a relatively short parallel guiding or through lumen located at its distal end and passing through the dilatation balloon. This design enables the short externally accessible monorail or guidewire lumen to be threaded over the proximal end of a pre-positioned guidewire without the need for docking a guidewire extension. Additionally, because the guidewire lumen is quite short the guidewire remains external to all portions of the catheter proximal to the distal portion of the catheter and frictional drag along the guidewire lumen reportedly is reduced. Thus, it is possible to recross an acutely closed lesion or to exchange balloon catheters without losing guidewire access or docking an extension wire.

However, in spite of this success a significant disadvantage associated with monorail dilatation catheters is the difficulty in steering the catheter along the guidewire through tortuous or convoluted vascular pathways. Because the guidewire is not supported within the catheter it is possible to wrap the distal end of the catheter around the guidewire as vascular curves and junctions are traversed. Additionally, though it is possible to remove the guidewire and leave the monorail catheter in position, it is virtually impossible to replace or exchange the guidewire if necessary as it is impossible to reengage the distal monorail guidewire lumen once it is positioned in the patient's body.

A more recent attempt at dealing with these problems is disclosed in U.S. Pat. No. 4,988,356 issued Jan. 29, 1991 to Crittenden et al. This catheter and guidewire exchange system utilizes a connector fitting mounted on the proximal end of the catheter and a longitudinal slit formed in the catheter shaft and extending from the proximal end proximate the connector forward towards the distal end. A guide member mounted on the fitting directs the guidewire through the slit and into the guidewire lumen in response to relative movement of the guidewire or catheter. This system reportedly avoids the need for a long exchange wire as well as the problems of a monorail design yet it presents several drawbacks of its own. First, the additional exchange fitting adds complexity to the design and function of the catheter. Further, the added drag induced by the fitting as it spreads the slit during catheter movement reduces the feel and control of the catheter as it is advanced along the guidewire. Moreover, because the slit terminates at a position distally to the proximal end of the catheter it is not possible to completely remove the catheter from the guidewire in a simple procedure. Reengagement of the catheter on the guidewire is even more complex.

Similarly, U.S. Pat. No. 4,748,982 issued Jun. 7, 1988 to Horzewski et al discloses a dilatation catheter having a slit guidewire sleeve running from the proximal end of its expandable balloon for approximately 30 centimeters. Thus, if the catheter is to be withdrawn it can be removed without utilizing an exchange or extension guidewire as the guidewire can be pulled out through the slit. Though simpler than the slit guidewire lumen disclosed in the patent to Crittenden et al, this catheter design also has drawbacks. For example, because the guidewire sleeve is slit bending the sleeve may open the slit and expose or possibly pinch the guidewire.

Accordingly, it is an object of the present invention to provide a dilatation balloon catheter design that can be fully exchanged easily without sacrificing guidewire access to a target lesion. A concurrent object of the present invention is to provide such a dilatation catheter that can traverse branched arteries and vascular curves and bends with the ease of an over-the-wire design.

It is a further object of the present invention to provide a dilatation catheter that facilitates the exchange or replacement of a guidewire if necessary.

It is yet an additional object of the present invention to provide a dilatation catheter with all of the advantages and features of an over-the-wire design that also provides the ability to be removed from a pre-positioned guidewire rapidly and simply without utilizing a guidewire extension or long exchange wire.

It is an additional object of the present invention to provide a fully exchangeable over-the-wire balloon catheter which will allow for catheter exchange without the need for docking a guidewire extension or utilizing a long exchange wire.

SUMMARY OF THE INVENTION

These and other objects are achieved by the fully exchangeable, dual lumen over-the-wire balloon catheter of the present invention which, in accordance with broad structural aspects thereof, includes two longitudinally aligned open lumens extending throughout the length of the catheter body. The shorter first lumen terminates at the proximal end of the dilatation balloon while the second lumen traverses the interior of the balloon and terminates at or slightly beyond the distal end of the balloon. Preferably, the catheter is formed with a longitudinal rip seam extending into the second lumen from the proximal end of the lumen along the majority of its length to a position proximal to the dilatation balloon.

This unique preferred construction allows the longer lumen to function as an over-the-wire guidewire lumen that can be removed from the proximal end of the guidewire with a simple peeling action to eliminate the need for a guidewire extension. Further, in the preferred embodiment of the present invention the rip seam terminates at or before a rigid or distally located side access port which may include a displacable gate to control guidewire routing through the guidewire lumen or side port. Accordingly, where desired, the cardiac physician may insert the externally accessible proximal end of the pre-positioned guidewire into the distal opening of the longer guidewire lumen through the dilatation balloon and back out through the side access port of the longitudinal rip seam to exchange the catheter without docking a guidewire extension or replacing the guidewire with a longer exchange wire. Thus, the dilatation catheter of the present invention provides all of the positioning and maneuverability advantages of a traditional over-the-wire catheter while it also provides for complete and uncomplicated catheter or guidewire exchangeability.

In an alternative embodiment of the present invention an additional side access port is provided at or near the proximal end of the rip seam, downstream of any Y-connector or fitting that may be mounted on the proximal end of the catheter. Thus, the rip seam will extend longitudinally along the catheter between the two side access holes. This alternative embodiment allows the vascular physician to utilize the catheter in several different manners.

For example, during initial placement of the device the guidewire can be threaded completely through the guidewire lumen from its distal opening to its proximal opening or, in the alternative, the proximal end of the guidewire may exit the proximal side access port. In either configuration the guidewire provides an added degree of pushability to the guidewire catheter combination during placement of the device. Should removal or exchange of the catheter be necessary this alternative construction utilizing the proximal side access port as an exit for the proximal end of the guidewire facilitates utilization of the rip seam and removal of the catheter by eliminating the need to remove any proximal fitting. Alternatively, where the guidewire traverses the entire length of the guidewire lumen any fitting or Y-connector must be detached prior to utilizing the rip seam.

As before, a replacement catheter may be threaded on to the externally accessible proximal end of the pre-positioned guidewire by threading the guidewire through the distal outlet of the second longer lumen and back out through the first or distal side access port. However, with this alternative embodiment the proximal end of the guidewire may be reinserted into the guidewire lumen through the second or proximal side access port and back out through the Y-connector or fitting in a "semi-over-the-wire configuration." In this configuration back bleeding is reduced during the procedure and wire movement is simplified.

Additionally, the second or proximal side access port facilitates the exchange of the guidewire should such a procedure be necessary. While the catheter is in place, the original guidewire can be removed through the Y-connector and a replacement guidewire can be inserted either through the Y-connector or through the proximal side access port into the second or guidewire lumen.

It should be noted that the guidewire operational advantages provided by the proximal side access port are available whether or not the catheter is provided with the rip seam. Thus, in an additional alternative embodiment of the present invention the guidewire lumen will simply include a distal and proximal side access port which may also be provided with partitions or gates to facilitate the control and routing of the guidewire through the catheter guidewire lumen. This combination of gated or non-gated side access ports allows the guidewire to be routed through the guidewire lumen in both an "over-the-wire" and "semi-over-the-wire" configuration and facilitates guidewire exchange.

When utilized, the rip seam in all embodiments may be formed by longitudinally weakening the wall of the catheter integral with the second longer guidewire lumen through any known manner including reduced wall thickness, partial transverse cutting, perforation, slitting or the like. Preferably, the rip seam will terminate in a side access port located proximally to the dilatation balloon and the guidewire lumen will be coaxially disposed within the first inflation lumen from at least this point onward to the distal end of the device.

This preferred coaxial construction of at least the distal portion of the catheter improves the maneuverability and reduces the profile of the device. Additionally, the distal portion of the catheter can be formed from relatively flexible low density materials as opposed to the preferably stiffer construction of the proximal majority of the device. Visual marking indices may be added to facilitate the location of the side access port and radiopaque markers may be incorporated adjacent to the inflation balloon as known in the art. Various stiffening elements including wires or a proximal hypotube may be incorporated into the apparatus or removably inserted into the first of second lumens to improve its pushability or, where gated side access ports are present, to assist in the functioning of the gates. However, such stiffening elements should be removable or configured to not interfere with the function of the rip seam.

Other features and advantages of the present invention will become apparent from the following detailed description, taken in conjunction with the accompanying drawings which illustrate, by way of example, the principles of the present invention.

BRIEF DESCRIPTION OF THE DRAWINGS

FIG. 1 is a partial fragmentary view in elevation of a fully exchangeable dual lumen over-the-wire dilatation catheter with a rip seam illustrating the principles of the present invention.

FIG. 2 is a sectional view of the dilatation catheter as seen along line 2—2 of FIG. 1.

FIG. 3 is a sectional view of the dilatation catheter as seen along the line 3—3 of FIG. 1.

FIG. 4 is a sectional view of the dilatation catheter as seen along the line 4—4 of FIG. 1.

FIG. 8 is a partial fragmentary top elevational view of an alternative embodiment of the fully exchangeable dual lumen over-the-wire catheter of the present invention illustrating additional features thereof.

FIG. 9 is an enlarged partial fragmentary view of a portion of the dilatation catheter of FIG. 8 illustrating an exemplary side access port.

FIG. 10 is an enlarged partial fragmentary view of a portion of the dilatation catheter of FIG. 8 illustrating a side access port in conjunction with an alternative guidewire placement.

FIG. 11 is a partial fragmentary perspective view of an alternative embodiment of the fully exchangeable dual lumen over-the-wire dilatation catheter of the present invention in combination with a guidewire.

FIG. 12 is a partial fragmentary perspective view of the alternative embodiment of FIG. 11 illustrating an alternative guidewire placement.

FIG. 13 is a partial fragmentary perspective view of an alternative embodiment of the dilatation catheter of the present invention in combination with a guidewire.

FIG. 14 is a partial fragmentary perspective view of the alternative embodiment of FIG. 13 illustrating an alternative guidewire placement.

FIG. 19 is an enlarged partial fragmentary view of a portion of a dilatation catheter illustrating the elements of a gated side port provided with a tapered cowling.

DETAILED DESCRIPTION

Figure 5:
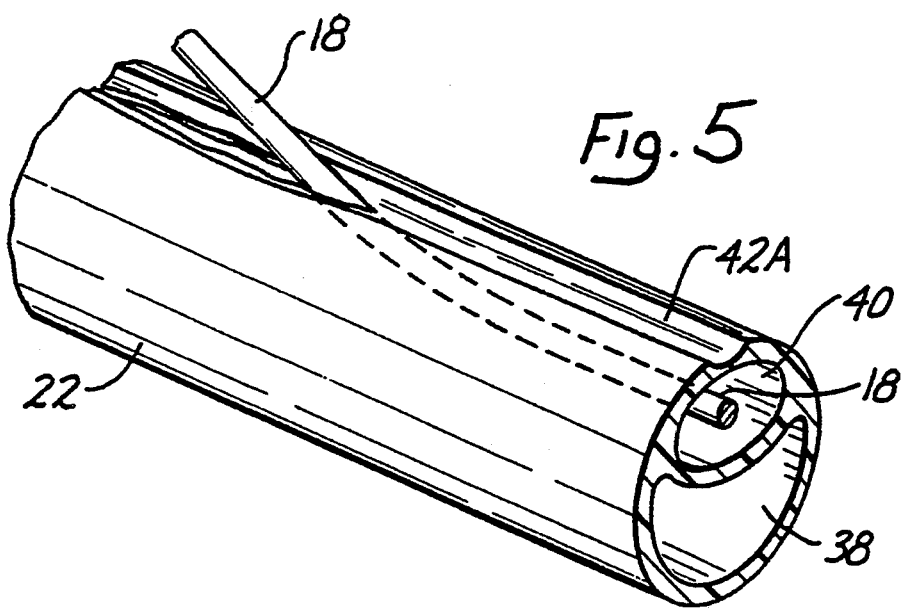
FIG. 5 is an enlarged partial fragmentary view of the fully exchangeable dual lumen over-the-wire dilatation catheter of the present invention in combination with a guidewire illustrating an embodiment of the rip seam.

Referring more particularly to the drawings in which similar elements are indicated by identical reference numerals. FIG. 1 illustrates an exemplary embodiment of the present invention including a catheter indicated generally by reference 10 mounted on a Y-connector 12 provided with an inflation port 14 and a compression hub 16 for sealing the catheter to Y-connector 12. A guidewire 18 extends proximally from Y-connector 12 and traverses the entire longitudinal extent of catheter 10. Catheter 10 includes an expandable or inflatable balloon 20 and a flexible, elongated tubular shaft 22 having a proximal end 24 adjacent compression hub 16 and a distal end 26 adjacent balloon 20. Though not essential to the practice of the present invention, catheter 10 also includes a tubular strain relief member 28 at its proximal end, depth markings 30 and 32 along the proximal portion of tubular shaft 22 and radiopaque marker 34 within balloon 20. Depth markings 30 and 32 enable the vascular physician to determine the relative positioning of catheter 10 within a patient while radiopaque marker 34 (formed of a precious metal such as gold or platinum) provides a clear visual image of the position of balloon 20 when viewed on a fluoroscope as known in the art.

Also, visible in FIG. 1 is fused joint 36 located along the distal portion of tubular shaft 22. As will be discussed in more detail below, though not essential to the practice of the present invention, it is preferred that the proximal majority of shaft 22 be formed of relatively high density material to enhance its stiffness and pushability. Similarly, it is preferred that the remaining distal portion of shaft 22 be formed of relatively low density material to increase its flexibility and maneuverability through tortuous vascular pathways such as the coronary arteries. Thus, fused joint 36 serves to bond these two materials together into a unitary construction. As those skilled in the art will appreciate, any form of medically acceptable secure joint is contemplated as being within the scope of the present invention while fusing the joint is preferred for manufacturing simplicity.

As shown in FIG. 2, catheter 10 is a dual lumen catheter provided with first and second lumens 38 and 40, respectively. Both lumens 38 and 40 extend throughout the longitudinal extent of tubular shaft 22 from proximal end 24 to distal end 26. Both lumens 38 and 40 are open at proximal end 24 and, in the exemplary embodiment of the present invention illustrated, first lumen 38 is connected in fluid conducting communication with inflation port 14 of Y-connector 12. At the distal end 26 of tubular shaft 22 first lumen 38 terminates in sealed fluid conducting communication with the interior of expandable balloon 20. Second lumen 40 is longer than first lumen 38 and is adapted to slidingly receive a guidewire 18 throughout its longitudinal extent from proximal end 24 and through the interior of expandable balloon 20. Thus, guidewire 18 is able to extend beyond both Y-connector 12 at the proximal end of catheter 10 and balloon 20 at the distal end of catheter 10.

Also visible in FIG. 2 is stiffening wire 41 positioned within first or inflation lumen 38. Stiffening wire 41 may be formed as a solid wire or hollow tube of an appropriately stiff material such as stainless steel having an exemplary outer diameter on the order of 0.008 inches. Preferably, stiffening wire 41 will be fused or secured to the internal wall of first lumen 38 at its proximal end and will extend along the length of first lumen 38 to a position beyond fused joint 36 located in the distal portion of tubular shaft 22. In this manner, stiffening wire 41 functions to add an additional degree of stiffness, pushability, and resistance to bending or kinking along the length of tubular shaft 22, particularly at areas that may be prone to deformation.

As more clearly illustrated in FIG. 2, first and second lumens 38 and 40 may be disposed in a parallel or bi-lateral arrangement or, as shown in FIG. 3, a coaxial arrangement with second lumen 40 disposed within first lumen 38. It is preferred that at least the distal portion of second lumen 40 be coaxially disposed within the distal portion of first lumen 38. However, it is contemplated as being within the scope of the present invention to configure the dual lumen construction of tubular shaft 22 as coaxial throughout its longitudinal extent or as a parallel or bi-lateral arrangement throughout its longitudinal extent. Similarly, it is also contemplated as being within the scope of the present invention to configure the dual lumen construction of tubular shaft 22 as coaxial within the proximal portion of tubular shaft 22 and parallel at the distal portion of tubular shaft 22. As those skilled in the art will appreciate, alternative arrangements also may be utilized. Nonetheless, regardless of the lumen arrangement utilized, following the distal termination of first lumen 38, second lumen 40 continues to traverse the interior of balloon 20 as illustrated in the sectional view of FIG. 4. In this manner, first lumen 38 functions as an inflation lumen for inflating and deflating balloon 20 while second lumen 40 functions as an over-the-wire guidewire lumen.

However, unlike conventional over-the-wire guidewire catheters, in one embodiment the catheter of the present invention is provided with a longitudinal rip seam 42 which extends into the second lumen 40 from the proximal end 24 of tubular shaft 22 to a position adjacent distal end 26. For example, in FIG. 1 rip seam 42 extends from proximal end 24 along shaft 22 (FIG. 2) to a position adjacent fused joint 36. Thus, as shown in FIGS. 2 and 3, rip seam 42 traverses the proximal majority of tubular shaft 22 yet is absent from the remaining distal portion thereof (FIG. 3). A wide variety of rip seam lengths and alternative embodiments of rip seam 42 are contemplated as being within the scope of the present invention.

Figure 6:
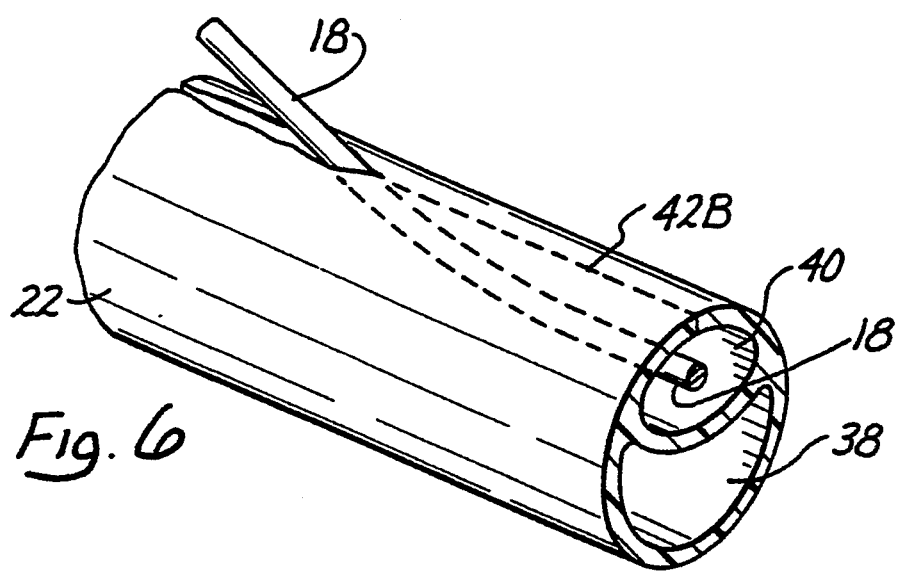
FIG. 6 is an enlarged partial fragmentary view of the fully exchangeable dual lumen dilatation catheter of the present invention in combination with a guidewire illustrating an alternative embodiment of the rip seam.
Figure 7:
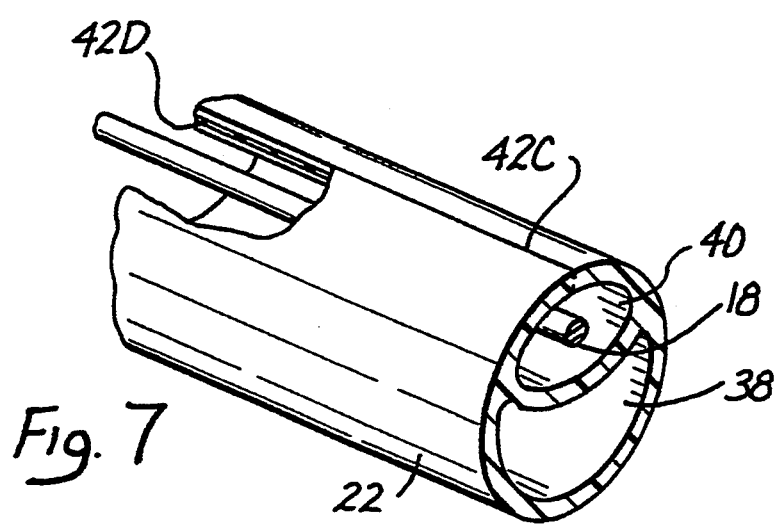
FIG. 7 is an enlarged partial fragmentary view of the fully exchangeable dual lumen dilatation catheter of the present invention in combination with a guidewire illustrating a still further alternative embodiment of the rip seam.

For example, the function of rip seam 42 is illustrated in the enlarged fragmentary view of FIG. 5. In FIG. 5 tubular shaft 22 of catheter 10 is shown being withdrawn along guidewire 18 by peeling the weakened wall material of reduced cross-sectional thickness wall material rip seam 42A from guidewire 18. Alternatively, in FIG. 6 rip seam 42B is formed from a longitudinally extending perforation through the wall material of second lumen 40. An additional alternative construction is illustrated in FIG. 7 where partial cuts 42C and 42D longitudinally extend along the wall of second lumen 40 in tubular shaft 22. Each partial cut 42C and 42D extends only part way through the wall thickness of second lumen 40. As those skilled in the art will appreciate, dual partial cuts are not essential to the practice of the present invention and a single partial cut will suffice to form rip seam 42. Each of the alternative forms of rip seam 42 functions in essentially the same manner allowing the vascular physician to withdraw catheter 10 along guidewire 18 by peeling guidewire 18 through rip seam 42.

In this manner, the over-the-wire dilatation catheter of the present invention provides the vascular physician with the ability to fully exchange the dilatation catheter without compromising guidewire access to a target lesion. For example, the fully exchangeable dilatation catheter 10 of the present invention may be inserted like a conventional over-the-wire catheter by threading the catheter guidewire lumen 40 along the guidewire 18 and advancing the catheter along a target vascular pathway to position the balloon 20 across a target lesion or stenosis. After the vascular physician has performed an angioplasty procedure by expanding and contracting the balloon across the stenosis the catheter may be withdrawn and removed from the patient by peeling the rip seam 42 from the proximal end of the guidewire positioned outside of the patient. By continuing to withdraw and peel the dilatation catheter along the guidewire the coaxial distal portion of the catheter may be removed from the patient and subsequently removed from the proximal portion of the guidewire without utilizing a docking extension or losing the positioning of the guidewire.

An additional feature of the present invention is illustrated in FIG. 8 where rip seam 42 is shown terminating at or near a side access port 54 in second lumen 40. Preferably, side access port 54 is located in a distal position along tubular shaft 22 remote from expandable balloon 20 at a point where second lumen 40 is directly adjacent to the wall of tubular shaft 22. For example, in FIG. 8 side access port 54 is positioned at fused joint 36. To assist the vascular physician in locating side access port 54, a distinctive visual marking 56 is provided to clearly indicate the position of side access port 54. It should be appreciated, that visual marking 56 is not essential to the practice to the present invention.

As illustrated in FIGS. 9 and 10, side access port 54 provides several additional advantages to the present invention. By clearly defining the distal termination of rip seam 42 side access port 54 provides the vascular physician with an additional degree of visual and tactile information regarding the progress of peeling guidewire 18 from second lumen 40 when withdrawing catheter 10 from a patient. Alternatively, should a vascular physician wish to exchange the dilatation catheter of the present invention with a second version having a different sized balloon 20 or to correct a nonfunctioning device, the physician may utilize side access port 54 as an exit from second lumen 40 to assist in threading catheter 10 onto the externally accessible end of guidewire 18 without the need for docking a guidewire extension. Thus, it is possible to remove and exchange the dilatation catheter of the present invention from a target vascular pathway by positioning and removing the catheter as previously discussed, then providing a second fully exchangeable dilatation catheter and threading the externally accessible proximal portion of the prepositioned guidewire through the distal portion of second lumen 40 and back outside access port 54, and then advancing this second catheter along the guidewire into position across the target stenosis.

An additional embodiment of the fully exchangeable over-the-wire dilatation catheter of the present invention is illustrated in FIGS. 11 and 12. In this embodiment a second or proximal side access port 58 is provided adjacent proximal end 24 of tubular shaft 22 and effectively defines the proximal termination of rip seam 42. As with side access port 54, proximal side access port 58 may be provided with its own visual marking 60 to aid in its location during utilization of catheter 10. As those skilled in the art will appreciate, angioplasty procedures are most often performed in darkened environments to enhance fluoroscopic visualization. Accordingly, visual markings 56 and 60, which may be formed in any manner known in the art including painting, etching, or embossing, may greatly assist the vascular physician in utilization of the apparatus.

In the alternative embodiment of the present invention illustrated in FIGS. 11 and 12 rip seam 42 longitudinally extends between side access ports 54 and 58 with a proximal termination distally of compression hub 16 on Y-connector 12. Accordingly, if desired, guidewire 18 may be threaded through second lumen 40 as previously described with the added ability to exit through second side access port 58 adjacent Y-connector 12. This configuration, as illustrated in FIG. 11, enables the vascular physician to remove catheter 10 from a patient by peeling rip seam 42 from guidewire 18 without removing Y-connector 12. Conversely, in the embodiment of the present invention illustrated in FIG. 1 removal of Y-connector 12 is necessary before catheter 10 can be removed from guidewire 18.

An additional advantage of this alternative embodiment of the present invention is provided by second side access port 58 in connection with the exchange of replacement of catheter 10 or guidewire 18. For example, after exchanging or replacing the dilatation catheter with a second such device, the proximal portion of guidewire 18 may be reinserted into second lumen 40 through second side access port 58 and out through Y-connector 12 as illustrated in FIG. 12. In this manner, a replacement dilatation catheter may be utilized in a semi-over-the-wire configuration with all of the advantages of an over-the-wire versus a monorail catheter design. Alternatively, should it become necessary to exchange or replace guidewire 18 while catheter 10 remains in position within a patient's body, after the original guidewire is removed a replacement wire can be inserted either through Y-connector 12 or second side access port 58 to load the guidewire into second lumen 40.

As shown in FIGS. 13 and 14, alternative embodiments of catheter 10 may be formed without rip seam 42. Preferably, these alternative embodiments are provided with both side access ports 54 and 58. This construction enables the vascular physician to direct guidewire 18 into proximal side access port 58 through second lumen 40 and past distal side access port 54 as illustrated in FIG. 13. Conversely, as illustrated in FIG. 14, guidewire 18 can be directed through second lumen 40 from the distal end of catheter 10 out through side access port 54 and back into second lumen 40 through proximal side access port 58 so that guidewire 18 exits Y-connector 12. Thus, this alternative embodiment of the present invention also provide the benefit of rapid and easy guidewire exchange in conjunction with the catheter positioning advantages provided by the semi-over-the-wire configuration.

Along these lines, it should be noted that for purposes of simplified guidewire exchange through second or proximal side access port 58 it is preferred that side access port 58 be positioned on catheter 10 at a point on catheter body 22 that will remain outside of the patient's body so that a replacement or exchange guidewire may be inserted through either Y-connector 12 or side access port 58. Conversely, in those situations where the maneuverability of the semi-over-the-wire configuration are desired it is preferred that side access port 58 be positioned more distally of Y-connector 12. Accordingly, it is contemplated as being within the scope of the present invention to position side access port 58 at locations ranging from approximately 5 cm to 35 cm from Y-connector 12.

Similarly, the preferred location of first or distal side access port 54 will range from approximately 5 cm to 30 cm from the proximal end of balloon 20. A preferred exemplary location for side access port 54 is 28 cm from the proximal end of balloon 20. This preferred location of side access port 54 enhances the tractability and maneuverability of distal end 26 of tubular shaft 22 when balloon 20 is being maneuvered toward a target lesion.

Figure 15:
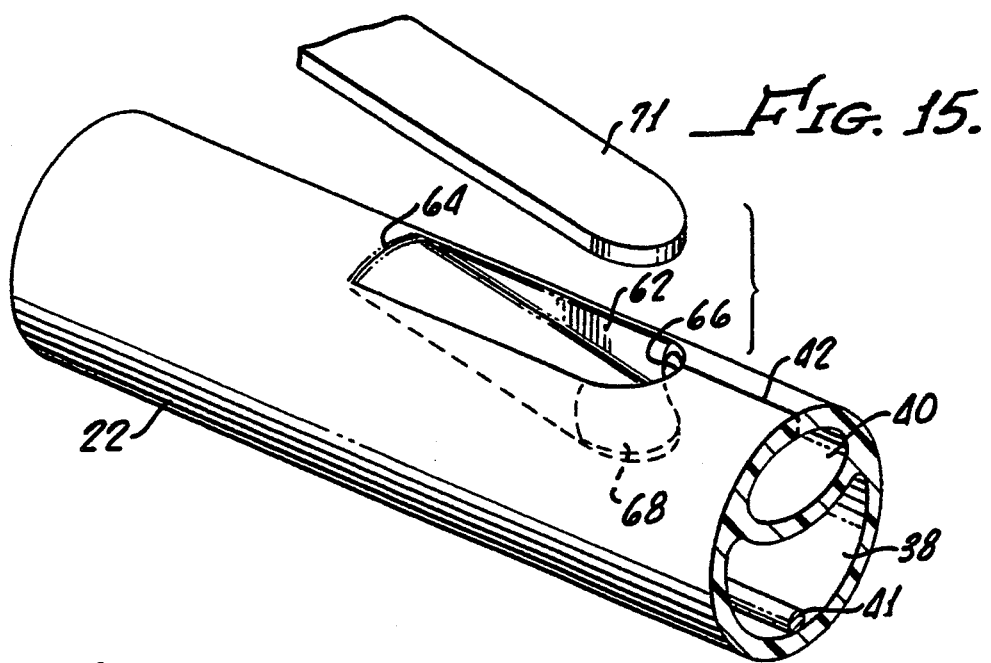
FIG. 15 is an enlarged partial fragmentary view of a portion of a dilatation catheter illustrating an exemplary gated side access port.

As an additional feature of the present invention, in order to facilitate the routing of guidewire 18 into, out of, and through second or guidewire lumen 40, several alternative side access port configurations are provided as illustrated in FIGS. 15-19. These alternative side access port constructions may be utilized as either distal side access port 54 or proximal side access port 58 or the like and significantly facilitate the vascular physician's ability to route or direct a guidewire or the like through the access port or the catheter lumen. More specifically, as illustrated in FIG. 15, gated side access port or opening 62 is provided in tubular shaft 22 in communication with second or guidewire lumen 40. Gated side port 62 is preferably a longitudinally disposed elongate opening as shown but may be configured in any convenient shape. For purposes of illustration, the longitudinally disposed opposing ends of gated side port 62 are identified as proximal end 64 and distal end 66. However, it should be appreciated by those skilled in the art that because alternative gated side port configuration 62 can be utilized as both a distal and proximal side port the relative positioning of longitudinally disposed ends 64 and 66 of gated side port 62 may be reversed or mirror images of that shown in FIGS. 15-18.

Gated side port 62 is provided with a partition 68 (shown in ghost in FIG. 15) which angularly extends longitudinally into guidewire lumen 40 from one of the opposed ends of gated side port 62 to a position within guidewire lumen 40 disposed adjacent to the other opposed end of gated side port 62. Thus, in FIGS. 15-18, partition 68 extends from proximal end 64 of gated side port 62 into second lumen 40 at an angle longitudinally along second lumen 40 to a position adjacent distal end 66 of gated side port 62. In this manner, partition 68 forms an angled ramp in gated side port 62. Partition 68 may be configured in varying degrees of flexibility ranging from relatively rigid to relatively freely displaceable. Regardless of the degree of rigidity, partition 68 will function to direct the routing of guidewire 18. However, when configured to be flexible, partition 68, by virtue of its ability to be displaced by a guidewire, functions as a gate or valve opening and closing gated side port 62 to direct guidewire 18 through or past port 62.

Figure 16:
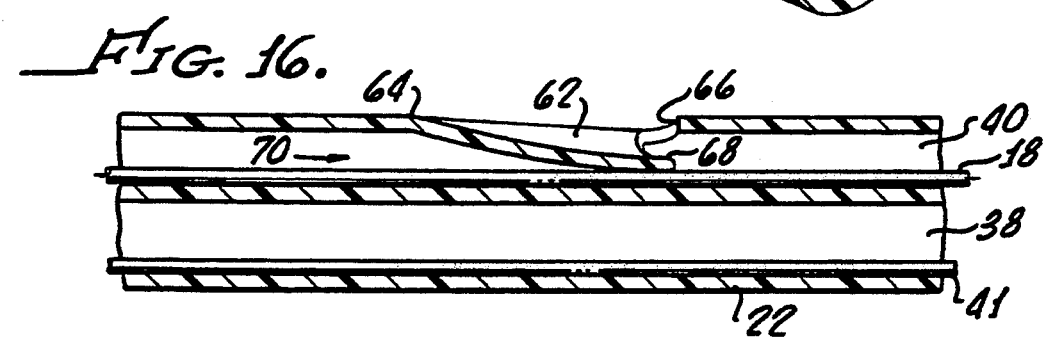
FIG. 16 is a longitudinal cross-section of a portion of the alternative dilatation catheter of FIG. 15 illustrating the function of the displacable gated side port during guidewire placement.
Figure 17:
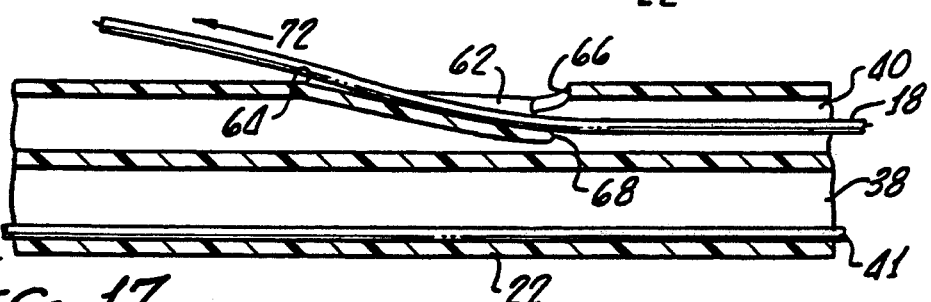
FIG. 17 is a longitudinal cross-section of a portion of the alternative dilatation catheter of FIG. 15 further illustrating the function of the displacable gated side port during an alternative guidewire placement.

The gated aspect of partition 68 is more clearly illustrated in FIGS. 16 and 17. As shown in FIG. 16, when guidewire 18 is moved through second lumen 40 past gated side port 62 in the direction of arrow 70 partition 68 functions to direct guidewire 18 past side port 62 and on through second lumen 40. Conversely, as illustrated in FIG. 17, when guidewire 18 is moved through second lumen 40 in the direction of arrow 72 partition 68 functions to close second lumen 40 and direct guidewire 18 out through gated side port 62. It should be noted that when partition 68 is configured to be relatively rigid, it may be necessary to insert a stiffening wire (not shown) into second lumen 40 to assist the functioning of the gated port. For example, referring first to FIG. 16 a stiffening wire analogous to guidewire 18 can be inserted second lumen 40 in the direction of arrow 70 until it contacts partition 68. Then, referring to FIG. 17, a guidewire 18 can be threaded through second lumen 40 in the direction of arrow 72 whereupon partition 68 will route guidewire 18 out through gated port 62.

As those skilled in the art will appreciate, the utilization of gated side access ports greatly facilitates the ability of a vascular physician to direct a guidewire through the guidewire lumen and out through the side access port. For example, as discussed above with respect to the embodiments of the present invention illustrated in FIGS. 11 through 14, if side access port 54 is replaced with gated side access port 62 then guidewire 18 can be advanced from Y-connector 12 or proximal side access port 58 through second lumen 40 and past distal side access port 54 as illustrated in FIGS. 11 and 13. Conversely, as illustrated in FIGS. 12 and 14, if guidewire 18 is directed through second lumen 40 from the distal end of catheter 10 the gated side access port will automatically direct guidewire 18 out through distal side port 54. This not only simplifies the guidewire routing procedure but also accelerates its progress. Additionally, if desired, the proximal side access port illustrated in FIGS. 11 through 14 can be configured to include an appropriately oriented partition 68 to direct guidewire 18 past or through proximal side access port 58, as desired.

Gated side access port 62 can be constructed using any of the currently available manufacturing techniques associated with catheters and similar devices. For example, a gated side access port can be formed in any portion of tubular shaft 22 by heating the identified portion of tubular shaft 22 to a softened forming temperature consistent with the characteristics of the material forming the walls of the tubular shaft. By angularly inserting a forming mandrel 71 as shown in FIG. 15 through the wall of tubular shaft 22 and into lumen 40 gated side access port 62 will be defined as partition 68 is formed from the deformation of the wall of tubular shaft 22 by forming mandrel 71. Allowing the heated portion to cool and removing forming mandrel 71 results in the formation of the gated side access port as shown. If desired, supporting mandrels corresponding to guidewire 18 and stiffening wire 41 as shown in FIG. 16 can be inserted prior to heating the portion of tubular shaft 22 corresponding to partition 68 and inserting forming mandrel 71. In this matter, the supporting mandrels will maintain the integrity of lumens 38 and 40 as partition 68 is deformed into position effectively bisecting a portion of lumen 40 by forming an angularly intersecting side port 62.

As those skilled in the art will appreciate, a variety of modifications of this methodology may be utilized to form the gated side access port of the present invention. Thus, it is possible to position the supporting and forming mandrel prior to heating the tubular shaft of the catheter. Additionally, simply inserting an appropriately configured heated mandrel such as mandrel 71 through the side wall of tubular shaft 22 into second lumen 40 will displace the wall material of tubular shaft 22, bisecting second lumen 40 and forming the angular flexible ramp of partition 68. Alternatively, where a conventional side access port already exists in communication with second lumen 40 a sleeve of material (not shown) can be bonded or heat fused (as known in the art) around tubular shaft 22 at the site of the opening and a mandrel utilized to displace the material into the appropriately longitudinally aligned angled ramp of partition 68. Alternatively, a separate tongue or reed may be bonded in place to form displacable partition 68.

Figure 18:
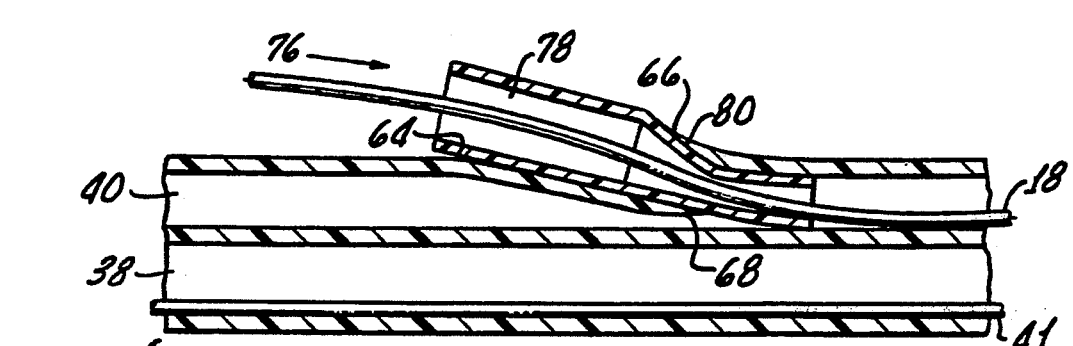
FIG. 18 is a longitudinal cross-section of a portion of an alternative dilatation catheter having a gated side port provided with a tapered cowling.

An alternative configuration of gated side access port 62 is illustrated in FIG. 18. There, gated side access port 62 is provided with an external guide cowling 74 for directing guidewire 18 into and through gated side access port 62 in the direction of arrow 76. Guide cowling 74 can be formed of an external sleeve or strip of material bonded or fused to the exterior of tubular shaft 22 and tapering in a direction roughly parallel to the orientation of partition 68. Thus, as shown in FIG. 18, external tapered guide cowling 74 tapers from proximal end 64 of gated side port 62 to a more narrow cross-section at distal end 66 of gated side port 62.

However, as illustrated in FIGS. 18 and 19 it is preferred that guide cowling 74 is formed by inserting and bonding a single lumen tube 78 into side access port 62. For example, as illustrated in FIG. 19 single lumen tube 78 is preferably formed with a tapered end 80 which is inserted into access port 62 and fused into position. Once fused in place, single lumen tube 78 will define both guide cowling 74 and partition 68. In this manner, second lumen 40 is bisected into a brief section having a dual lumen configuration.

Any of the known catheter forming and bonding steps may be utilized to form gated side access port 62 and/or guide cowling 74. Utilizing guide cowling 74 enables the vascular physician to readily insert guidewire 18 through gated side access port 62 and into second lumen 40. As those skilled in the art will appreciate, tapered guide cowling 74 may be utilized with the previously discussed configurations of non-gated side access ports if desired. Similarly, alternative guide cowling configurations may be utilized which taper from distal end 66 toward proximal end 64 of gated access port 62 when displacable partition 68 is similarly oriented. Preferably, guide cowling 74 will be formed of flexible material similar to that of catheter 10 or balloon 20 and will be configured so as not to interfere with the normal operation of the catheter.

As previously noted, each of the embodiments of the present invention discussed herein may be formed from a variety of surgically acceptable flexible materials as known in the art. However, it is preferred that the proximal portion of tubular shaft 22 be formed of a relatively high density material such as polyethylene or polypropylene to provide added pushability and control in placing the catheter within a vascular pathway. For enhanced flexibility and maneuverability at the distal end of the catheter it is preferred that the remaining distal portion of the tubular shaft be formed of relatively low density material such as polyethylene or polypropylene. These two materials may be fused by thermal bonding to form the previously discussed fused joint 36. Preferably, fused joint 36 will be located approximately 30 cm from balloon 20 on an exemplary catheter having an overall length ranging from approximately 100 cm to 160 cm.

Additionally, it should be appreciated that various stiffening elements may be utilized in conjunction with the dilatation catheter of the present invention as discussed above. For example, the proximal portion of tubular shaft 22 may be stiffened utilizing wires or flexible metal tubes known as "hypotubes" (not shown) which are disposed along its longitudinal extent. It should be appreciated that these exemplary materials, dimensions and construction techniques are illustrative of the principles of the present invention and that other alternative materials, dimensions and construction techniques may be utilized within the scope of the present invention.

In closing it is to be understood that the embodiments of the invention disclosed herein are illustrative of the principles of the invention and that other modifications may be employed which are within the scope thereof. Thus, by way of example, but not of limitation, the rip seam may be opened with a cutting instrument located on the Y-connector or an external fitting in a manner that will open the second guidewire lumen as the catheter is removed along the guidewire. Accordingly, the present invention is not limited to that precisely as shown and described in the specification.

What is claimed:

1. A fully exchangeable over-the-wire dilatation catheter comprising:
    an expandable balloon;
    a flexible, elongate tubular shaft having a proximal end, a distal end, and first and second through lumens, each of said lumens in open extension from said proximal end to said distal end, said first lumen terminating in sealed fluid conducting communication with the interior of said expandable balloon at said distal end of said tubular shaft, said second lumen adapted to slidingly receive a guidewire throughout its longitudinal extent from said proximal end to said distal end and through said interior of said expandable balloon;
    a longitudinal rip seam provided in said tubular shaft and extending into said second lumen along at least a portion of the longitudinal extent of said second lumen;
    a first gated side access port in communication with said second lumen, disposed near said distal end proximal to said balloon and provided with a partition angularly extending longitudinally into said second lumen; and
    a second gated side access port in communication with said second lumen, disposed near said proximal end.

2. The fully exchangeable over-the-wire catheter of claim 1 wherein said inflation lumen is provided with a stiffening element.

3. The fully exchangeable over-the-wire dilatation catheter of claim 1 wherein said first gated side access port has a proximal end and a distal end and said partition angularly extends longitudinally into said second lumen from said proximal end of said first access port to a position within said second lumen disposed adjacent to said distal end of said first access port.

4. The fully exchangeable over-the-wire dilatation catheter of claim 1 wherein said first gated side access port has a proximal end and a distal end and said partition angularly extends longitudinally into said second lumen from said distal end of said first access port to a position within said second lumen disposed adjacent to said proximal end of said access port.

5. The fully exchangeable over-the-wire catheter of claim 1 wherein said guidewire lumen and said inflation lumen are disposed in parallel throughout the longitudinal extent of said flexible, elongate tubular shaft.

6. The fully exchangeable over-the-wire catheter of claim 1 wherein said guidewire lumen and said inflation lumen are coaxially disposed throughout the longitudinal extent of said flexible, elongate tubular shaft.

7. The fully exchangeable over-the-wire dilatation catheter of claim 1 wherein at least the distal portion of said second lumen is coaxially disposed within said first lumen.

8. The fully exchangeable over-the-wire catheter of claim 1 wherein at least the proximal portion of said guidewire lumen is coaxially disposed within said inflation lumen.

9. The fully exchangeable over-the-wire catheter of claim 1 wherein at least the distal portion of said guidewire lumen is disposed in parallel with said inflation lumen.

10. The fully exchangeable over-the-wire catheter of claim 1 wherein at least the proximal portion of said guidewire lumen is disposed in parallel with said inflation lumen.

11. The fully exchangeable over-the-wire dilatation catheter of claim 1 wherein the distal portion of said flexible, elongate tubular shaft is formed of relatively low density material to provide added flexibility and maneuverability.

12. The fully exchangeable over-the-wire catheter of claim 1 wherein said of said gated side access ports is provided with an external tapered guide cowling for directing a guidewire through said side access port.

13. The fully exchangeable over-the-wire dilation catheter of claim 1 wherein said second gated side access port has a proximal end and a distal end and said partition angularly extends longitudinally into said second lumen from said proximal end of said second access port to a position within said second lumen disposed adjacent to said distal end of said second access port.

14. A gated side access port for controlling the routing of a guidewire or the like in a lumen, said access port comprising:
an external side opening in communication with said lumen and having opposed proximal and distal ends longitudinally disposed along said lumen;
a partition angularly extending longitudinally into said lumen from one of said opposed ends of said side opening to a position within said lumen disposed adjacent to the other of said opposed ends of said side opening; and
an external tapered guide cowling for directing a guidewire or the like through said side access port.

15. The gated side access port of claim 14 wherein said external guide cowling tapers from said proximal end of said side opening to said distal end of said side opening for directing a guidewire through said side access port.

16. The gated side access port of claim 14 wherein said external guide cowling tapers from said distal end of said side opening to said proximal end of said side opening for directing a guidewire through said side access port.

17. An external guide cowling for directing a guidewire or the like into a catheter guidewire side access port, said guide cowling comprising:
a tapered partition defining an angularly disposed opening adjacent to one end of said side port, said partition tapering to a position adjacent the other end of said side port.

18. A method for forming a gated side access port in a catheter having a flexible, elongate tubular shaft provided with at least one through lumen, said method comprising the steps of:
creating a side opening through said tubular shaft into said lumen;
angularly inserting a short section of tubing into said opening; and
permanently affixing said tubing within said opening.

19. A fully exchangeable over-the-wire dilatation catheter comprising:
an expandable balloon;
a flexible, elongate tubular shaft having a proximal end, a distal end, and first and second through lumens, each of said lumens in open extension from said proximal end to said distal end, said first lumen terminating in sealed fluid conducting communication with the interior of said expandable balloon at said distal end of said tubular shaft, said second lumen adapted to slidingly receive a guidewire throughout its longitudinal extent from said proximal end to said distal end and through said interior of said expandable balloon;
a distal side access port in communication with said second lumen; and
a proximal side access port in communication with said second lumen.

20. The fully exchangeable over-the-wire dilatation catheter of claim 19 wherein said distal side access port is gated with a partition angularly extending longitudinally into said second lumen.

21. The fully exchangeable over-the-wire dilatation catheter of claim 19 wherein said proximal side access port is gated with a partition angularly extending longitudinally into said second lumen.

22. A method for positioning a semi-over-the-wire dilatation catheter on a guidewire positioned within a target vascular pathway of a patient and having a proximal guidewire portion located outside of said patient, said method comprising the steps of:
threading said proximal guidewire portion into the distal end of the second lumen of the catheter of claim 36 and out through the distal side access port of said catheter;
advancing said catheter along said guidewire and into said patient; and
threading said proximal portion of said guidewire into the proximal side access port of said catheter and out through the proximal end of said second lumen.

23. A method of exchanging a guidewire in a catheter positioned within a target vascular pathway of a patient, said method comprising the steps of:
threading a first guidewire through the second lumen of the dilatation catheter of claim 36;
positioning said first guidewire and dilatation catheter combination within the target vascular pathway of a patient so that the proximal side access port of said catheter remains outside said patient;
removing said first guidewire from said catheter; and
threading a second guidewire into said proximal side access port and through said second lumen.

* * * * *